(12) United States Patent
Vodinh

(10) Patent No.: US 10,231,752 B2
(45) Date of Patent: Mar. 19, 2019

(54) SCALPEL HANDLE HAVING A BLADE SHIELD UTILIZING OVER CENTER SPRING

(71) Applicant: Hien Vodinh, Knoxville, TN (US)

(72) Inventor: Hien Vodinh, Knoxville, TN (US)

(73) Assignee: Bosela Design LLC, Chattanooga, TN (US)

( * ) Notice: Subject to any disclaimer, the term of this patent is extended or adjusted under 35 U.S.C. 154(b) by 32 days.

(21) Appl. No.: 15/731,787

(22) Filed: Aug. 1, 2017

(65) Prior Publication Data

US 2017/0333069 A1 Nov. 23, 2017

Related U.S. Application Data

(63) Continuation-in-part of application No. 14/544,969, filed on Mar. 10, 2015, now Pat. No. 9,757,146, which is a continuation-in-part of application No. 13/998,559, filed on Nov. 8, 2013, now Pat. No. 9,027,254.

(51) Int. Cl.
| | |
|---|---|
| *A61B 17/3213* | (2006.01) |
| *B26B 29/02* | (2006.01) |
| *A61B 17/3211* | (2006.01) |
| *A61B 17/00* | (2006.01) |
| *A61B 90/00* | (2016.01) |

(52) U.S. Cl.
CPC .......... *A61B 17/3213* (2013.01); *B26B 29/02* (2013.01); *A61B 2017/0023* (2013.01); *A61B 2017/0046* (2013.01); *A61B 2017/00367* (2013.01); *A61B 2017/00862* (2013.01); *A61B 2017/32113* (2013.01); *A61B 2090/034* (2016.02)

(58) Field of Classification Search
CPC ............ A61B 17/3211; A61B 17/3213; A61B 2017/3213; A61B 2017/3211; B26B 29/04
USPC .............. 30/2, 151, 153, 161, 162, 294, 286
See application file for complete search history.

(56) References Cited

U.S. PATENT DOCUMENTS

| | | |
|---|---|---|
| 273,981 A | 3/1883 | Glovers |
| 942,342 A | 12/1909 | McNally |
| 1,452,893 A | 4/1923 | Porth |
| 1,810,593 A | 6/1931 | Brown |
| 2,428,742 A | 10/1947 | Rothe |
| 3,457,383 A | 7/1969 | Roberts, Jr. et al. |

(Continued)

*Primary Examiner* — Sean M Michalski
*Assistant Examiner* — Fernando A Ayala
(74) *Attorney, Agent, or Firm* — Michael E. McKee

(57) ABSTRACT

A scalpel handle for holding a blade includes a handle member and a finger-operable actuator having a blade shield portion. The actuator is mounted upon the handle member for movement relative thereto between a first condition at which the blade shield portion covers the edge of the blade and a second condition at which the blade shield portion is disposed in out-of-the-way position so that by moving the actuator between the first and second conditions, the blade shield portion is moved between its blade-covering and its out-of-the-way positions. An over center spring is interposed between the actuator and the handle member so that upon movement of the actuator into its second condition, the blade shield portion is biased into the out-of-the-way position and so that upon movement of the actuator into its first condition, the blade shield portion is biased into the blade-covering position.

20 Claims, 8 Drawing Sheets

(56) References Cited

U.S. PATENT DOCUMENTS

| | | | |
|---|---|---|---|
| 3,781,988 A | | 1/1974 | Jones |
| 4,006,868 A | * | 2/1977 | Hochradel ............. B65G 51/06 |
| | | | 406/186 |
| 4,513,761 A | | 4/1985 | Van Deursen |
| 4,980,977 A | | 1/1991 | Matin et al. |
| 5,139,507 A | | 8/1992 | Dolgin et al. |
| 5,250,064 A | | 10/1993 | Schneider |
| 5,440,814 A | * | 8/1995 | Hall ......................... B26B 3/06 |
| | | | 30/286 |
| 6,178,640 B1 | | 1/2001 | Votolato |
| 6,718,637 B1 | | 4/2004 | Ortner |
| 7,024,772 B1 | | 4/2006 | Shaver et al. |
| 7,485,126 B2 | | 2/2009 | Adelman et al. |
| 7,509,742 B2 | | 3/2009 | Votolato |
| 7,810,241 B2 | | 10/2010 | Pooler |
| 8,347,509 B2 | | 1/2013 | Votolato |
| 8,671,578 B1 | | 3/2014 | Frazer |
| 9,027,254 B1 | | 5/2015 | Vodinh |
| 2002/0188309 A1 | | 12/2002 | Adelman |
| 2007/0276422 A1 | * | 11/2007 | Pooler ................. A61B 17/3211 |
| | | | 606/167 |
| 2011/0119925 A1 | | 5/2011 | Rohrbach |
| 2012/0279071 A1 | | 11/2012 | Garavaglia et al. |
| 2012/0317820 A1 | | 12/2012 | McGushion et al. |
| 2013/0185943 A1 | | 7/2013 | Landwehr |
| 2013/0326884 A1 | | 12/2013 | Harvey |
| 2014/0155202 A1 | | 6/2014 | Young |

* cited by examiner

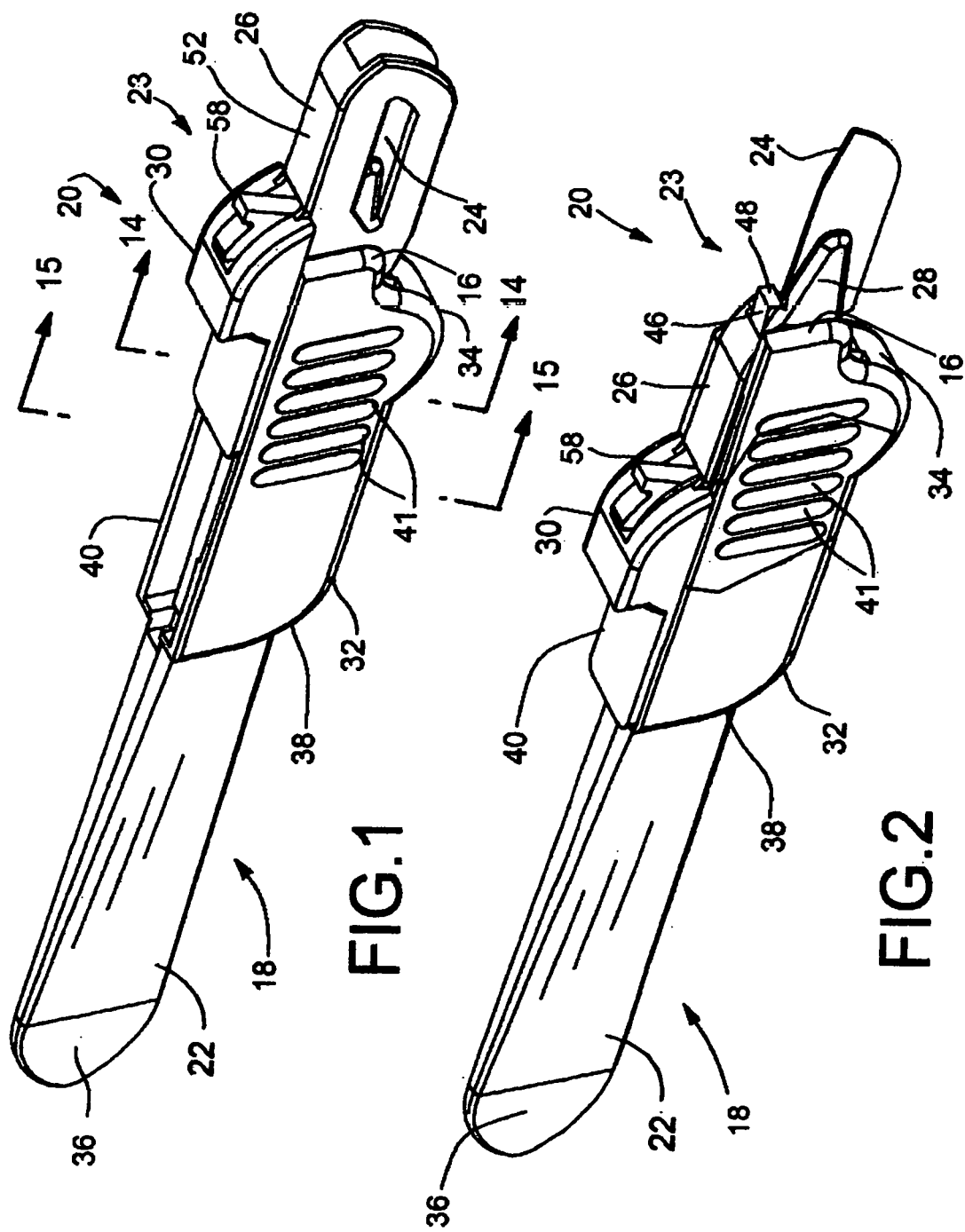

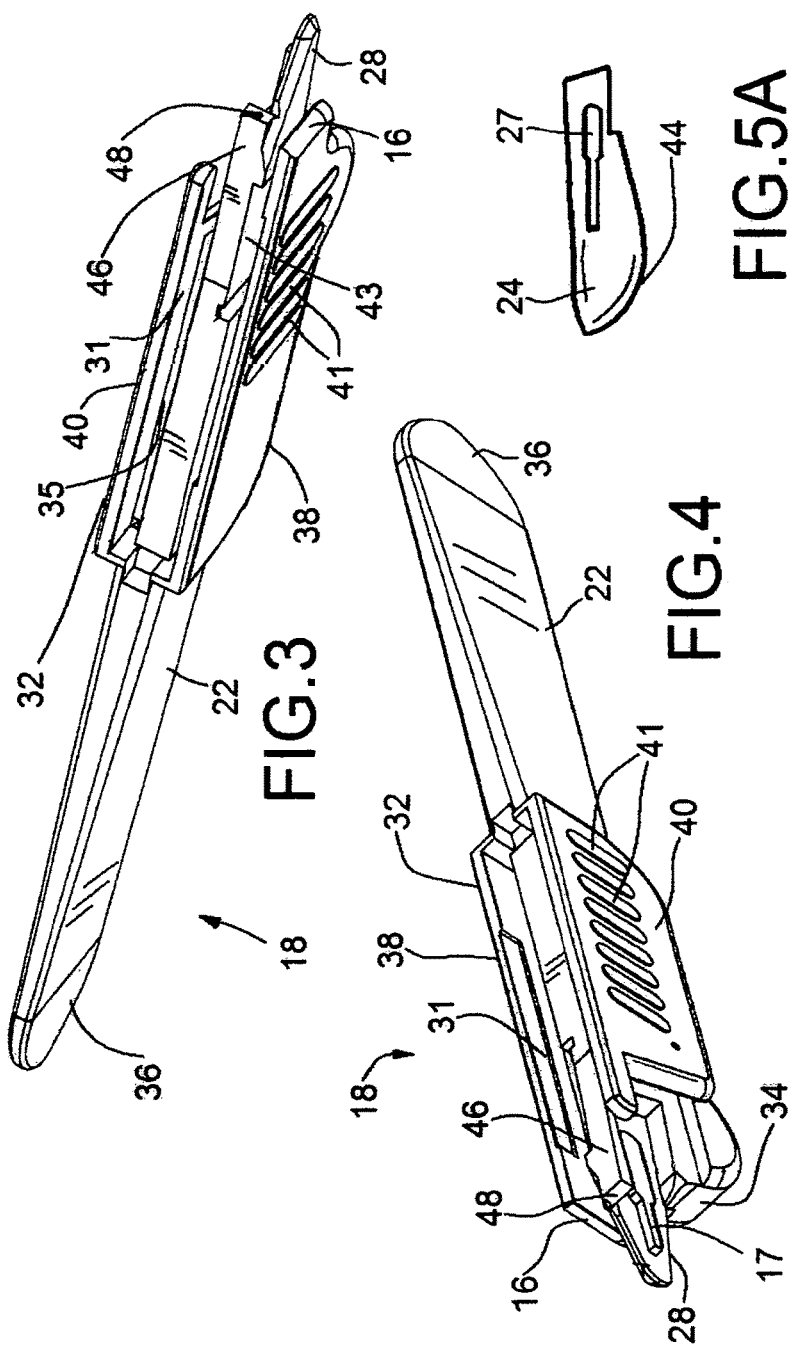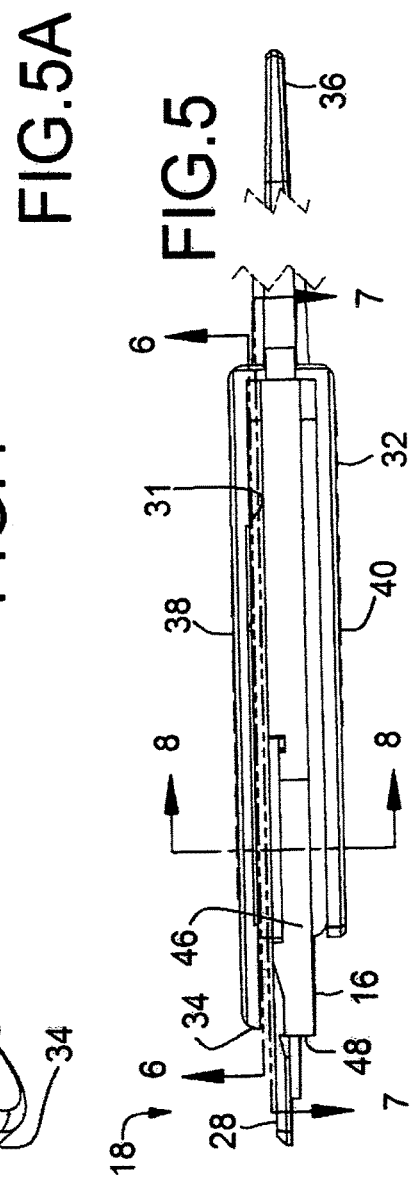

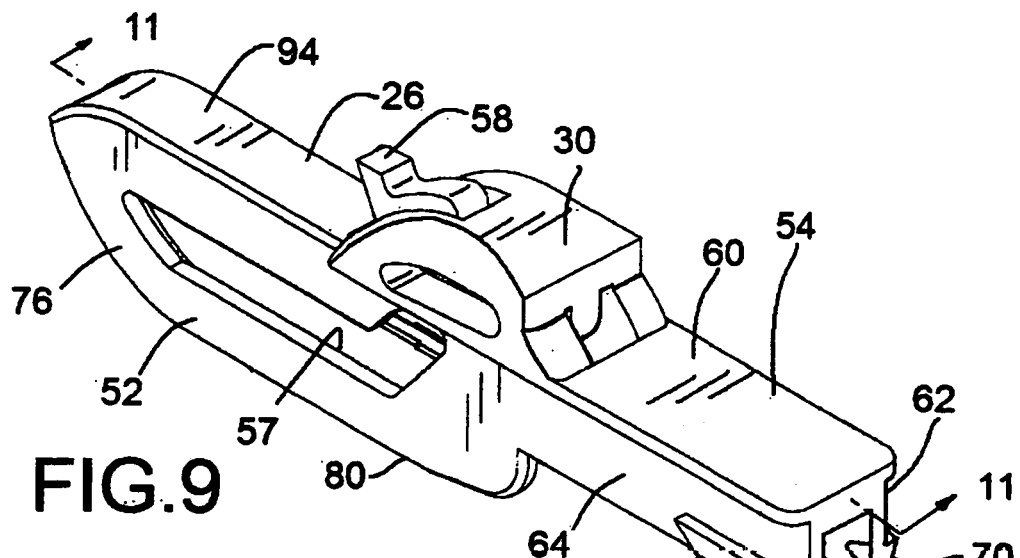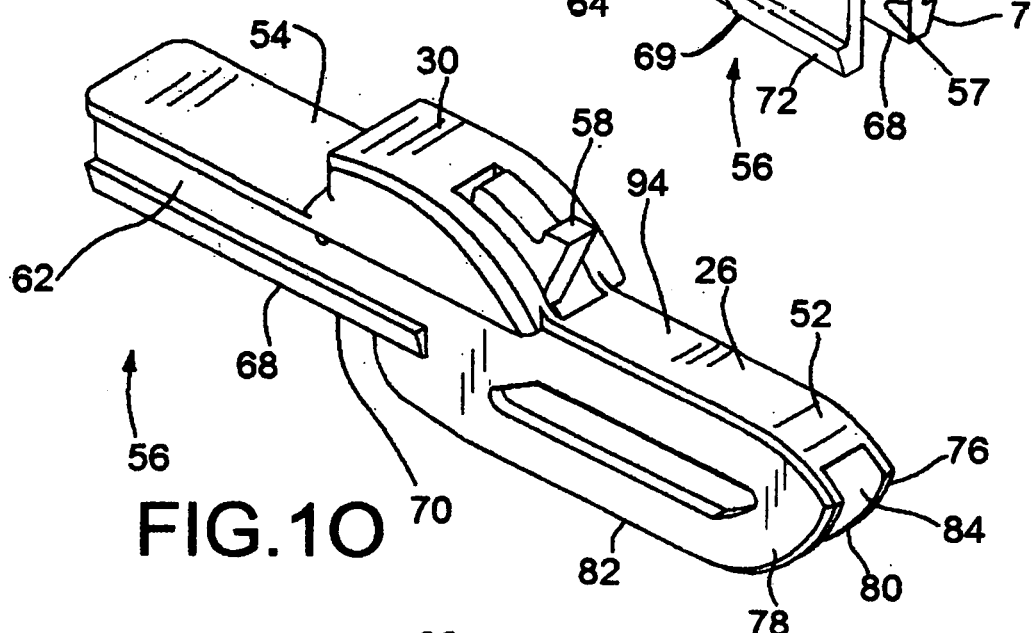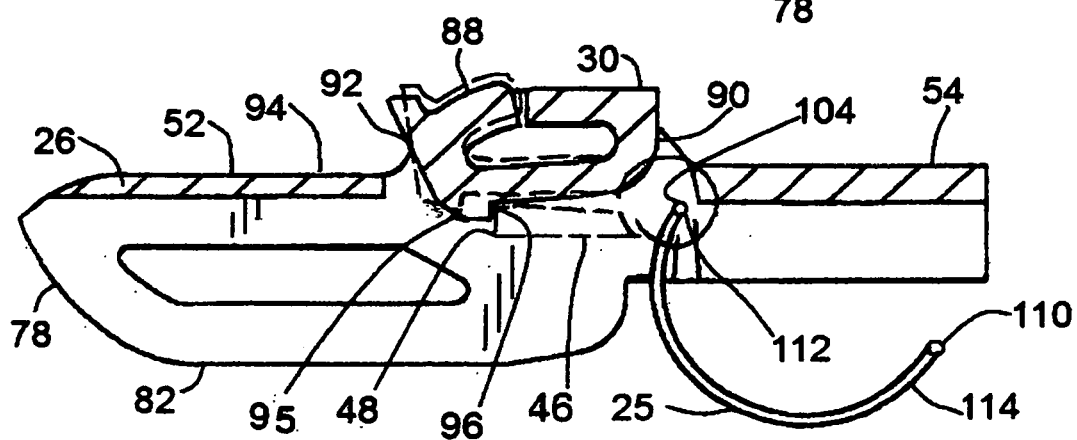

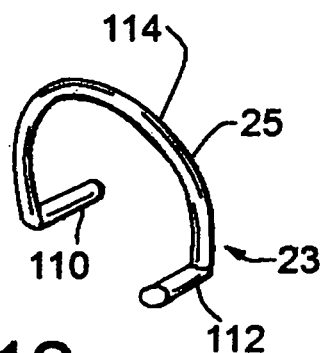
FIG.12
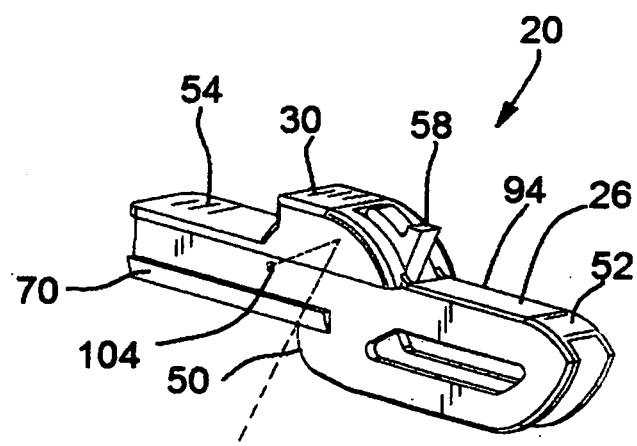
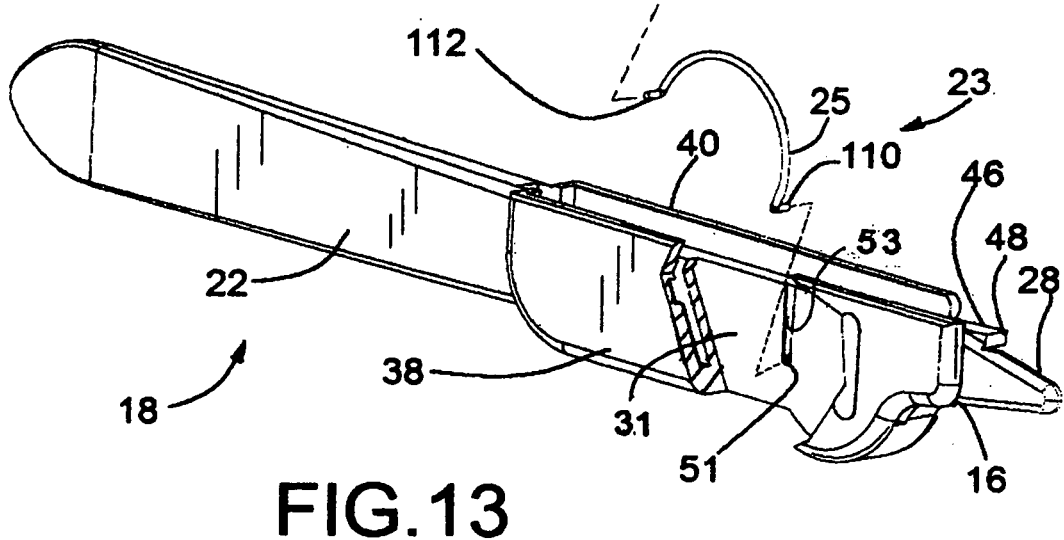
FIG.13

SCALPEL HANDLE HAVING A BLADE SHIELD UTILIZING OVER CENTER SPRING

This application is a continuation-in-part of application Ser. No. 14/544,969, filed Mar. 10, 2015 and entitled SCALPEL HANDLE HAVING A BLADE SHIELD UTILIZING OVER CENTER SPRING which is a continuation-in-part of an earlier application Ser. No. 13/998,559, filed Nov. 8, 2013, now U.S. Pat. No. 9,027,254 and entitled SCALPEL HANDLE HAVING A BLADE SHIELD, each of which is incorporated herein by reference.

BACKGROUND OF THE INVENTION

This invention relates generally to surgical scalpels and relates, more particularly, to means and methods by which the cutting edge of a scalpel blade is covered between periods of use.

It is known that in order to reduce the risk of inadvertent cuts from a scalpel in a surgical environment as, for example, the scalpel is passed from one individual to another, the cutting blade of the scalpel can be covered with a safety shield between periods of use, and it is this class of shielded scalpels to which the present invention is to be compared. One such shielded scalpel is described in my U.S. Pat. No. 9,027,254 as having an elongated handle, a cutting blade which extends from the handle and a safety shield which is attached to the handle for movement relative thereto between a blade edge-covering position and an out-of-the way position at which the cutting edge of the blade is exposed for use. Furthermore, a manually-operable actuator mechanism is mounted upon the handle for manipulation of the actuator mechanism relative to the handle between first and second conditions, and other mechanisms (e.g. linkages) are interposed between the actuator mechanism and the safety shield so that the movement of the shield between its edge-covering and out-of-the-way positions is effected by the movement of the actuator mechanism relative to the handle between its first and second conditions.

A limitation associated with shielded scalpel designs of the prior art relates to the schemes by which the blade shields are held in place in each of its blade-covering position and its out-of-the-way position. In particular, such shielded scalpel designs commonly rely upon a closely-controlled fit-up between adjacent components of the scalpel design to ensure that the blade shield is maintained in each of its blade-covering position and its out-of-the-way position. In other words, if the fit-up between adjacent components of the scalpel design is too loose (resulting, for example, from tolerance error during manufacture of the scalpel components), the blade shield is not likely to be firmly held in its blade-covering position when the actuator mechanism is moved into its first condition and also be firmly held in its blade-covering condition when the actuator mechanism is moved to its second condition.

It would be desirable to provide a scalpel handle whose safety shield is urged into its blade-covering condition when the actuator mechanism is manually moved into its first condition and is urged into its out-of-the-way condition when the actuator mechanism is manually moved into its second condition.

Accordingly, it is an object of the present invention to provide a new and improved scalpel handle having a safety shield for covering the blade mounted upon the handle.

Another object of the present invention is to provide such a scalpel handle having a safety shield which is movable between a blade-covering position and an out-of-the-way position at which the cutting edge of the blade is exposed for use and which employs an improved scheme for firmly holding the shield in each of its blade-covering position and its out-of-the-way position.

Still another object of the present invention is to provide such a scalpel handle whose shield is urged into its blade-covering position when the actuator mechanism is moved toward the position assumed when in its first condition and is also urged into its out-of-the-way position when the actuator mechanism is moved toward the position assumed when in its second condition.

Yet another object of the present invention is to provide such a scalpel handle whose shield can be readily moved by an operator between its blade-covering and its out-of-the-way position.

A further object of the present invention is to provide such a scalpel handle having an actuator mechanism which can be manipulated by a finger (e.g. the index finger) of the hand which grasps the handle for moving the blade shield between its blade-covering position and its out-of-the-way position.

A still further object of the present invention is to provide such a scalpel handle whose actuator mechanism can be manipulated between first and second conditions for moving the blade shield between its blade-covering position and its out-of-the-way position and whose actuator mechanism is biased into the position assumed when in its first condition and is biased into the position assumed when in its second condition.

A yet further object of the present invention is to provide such a scalpel handle which is comprised of relatively few components.

One more object of the present invention is to provide such a scalpel handle whose actuator mechanism and blade shield are integrally joined as a single component.

Still one more object of the present invention is to provide such a scalpel handle including a safety latch for releasably locking the blade shield in its blade-covering condition.

Yet one more object of the present invention is to provide such a scalpel handle which is uncomplicated in structure, yet effective in operation.

SUMMARY OF THE INVENTION

This invention resides in a scalpel handle for holding a blade having a cutting edge.

The scalpel handle includes a handle member to which a blade is securable for use and a manually-operable actuator mechanism having a blade shield portion which is mounted upon the handle member for movement relative thereto between a first condition and a second condition and along a substantially linear path of movement so that when a blade is secured to the handle member and the actuator mechanism is positioned in the first condition, the blade shield portion is positioned in a blade-covering position at which the cutting edge of the blade is covered by the blade shield portion and when the actuator mechanism is positioned in the second condition, the blade shield portion is positioned in an out-of-the-way position which exposes the cutting edge of the blade for use. The scalpel handle further includes an over center spring having two opposite end portions and being interposed between the actuator mechanism and the handle member so that upon movement of the actuator mechanism from the first condition into the position assumed by the actuator mechanism when in the second condition, the blade shield portion is biased by the over center spring into the blade-exposing position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield portion is biased by the over center spring into the blade-covering position and the over center spring resists movement of the actuator mechanism from the first condition toward the position assumed by the actuator mechanism when in the second condition. One end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the substantially linear path of movement, the one end portion of the over center spring also moves along a substantially linear path of movement.

BRIEF DESCRIPTION OF THE DRAWINGS

FIG. 1 is a perspective view of a scalpel assembly within which features of the present invention are embodied and illustrating the blade shield portion of the actuator mechanism of the assembly when disposed in a blade-covering position.

FIG. 2 is a perspective view of the FIG. 1 scalpel assembly similar to that of FIG. 1, but illustrating the blade shield portion of the actuator mechanism of the assembly when disposed in an out-of-the-way position.

FIG. 3 is a perspective view of the handle member of the FIG. 1 assembly.

FIG. 4 is a perspective view of the handle member of the FIG. 1 assembly, as seen from an alternative angle.

FIG. 5 is a top plan view of the handle member of the FIG. 1 assembly as seen generally from above in FIG. 4.

FIG. 5a is a side elevation view of the blade utilized in the FIG. 1 assembly.

FIG. 9 is a perspective view of the actuator mechanism of the FIG. 1 assembly.

FIG. 10 is a perspective view of the actuator mechanism of the FIG. 1 assembly, as seen from an alternative angle.

FIG. 11 is a longitudinal cross-sectional view of a fragment of the actuator mechanism of the FIG. 1 assembly taken along line 11-11 of FIG. 9 and depicting one end of the over center spring being connected to the actuator mechanism.

FIG. 12 is a perspective view of the over center spring utilized in the FIG. 1 assembly.

FIG. 13 is a perspective view of the components of the FIG. 1 assembly, shown before assembly and partially cut-away.

Figure 6:
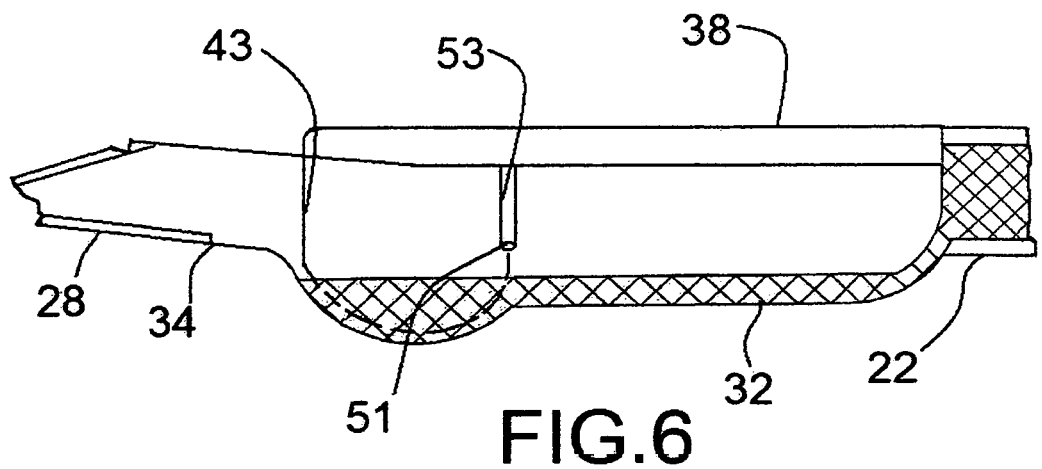
FIG. 6 is a longitudinal cross-sectional view of a fragment of the handle member of the FIG. 1 assembly taken along line 6-6 of FIG. 5.

DETAILED DESCRIPTION OF AN
ILLUSTRATIVE EMBODIMENT

Turning now to the drawings in greater detail and considering first FIGS. 1 and 2, there is illustrated an embodiment, generally indicated 20, of a scalpel, or scalpel assembly, within which features of the present invention are embodied. Briefly, the scalpel 20 includes means, generally indicated 18, providing a handle of the scalpel 20 and an elongated blade 24 which is connected to the handle-providing means 18. The handle-providing means 18 of the depicted scalpel 20 includes an elongated handle member 22 having a forward end 16 to which the elongated blade 24 is fixedly secured, and the scalpel 20 further includes a manually-operable actuator mechanism 30 having a blade shield portion 26 which is joined to the handle member 22 for sliding movement therealong between a first condition, or position, as illustrated in FIG. 1, at which the blade shield portion 26 of the actuator mechanism 30 covers, and thereby protects, the cutting edge of the blade 24 and a second condition, or position, as illustrated in FIG. 2, at which the blade shield portion 26 is moved rearwardly (relative to the handle member 22) of its FIG. 1 position to an out-of-the-way position (as viewed in FIG. 2) so that the cutting edge of the blade 24 is exposed for use.

The invention described herein can be embodied in both reusable or disposable scalpels. Accordingly, the principles of the present invention can be variously applied.

The scalpel 20 also includes mechanical biasing means, generally indicated 23 in FIGS. 1 and 2, which is interposed between the actuator mechanism 30 and the handle member 22 for biasing the actuator mechanism 30 (and thus the blade shield portion 26) into its FIG. 1 first condition as the actuator mechanism 30 is moved from its FIG. 2 second condition and into relatively close proximity to the position assumed when the actuator mechanism 30 is positioned in its FIG. 1 first condition and for biasing the actuator mechanism 30 (and thus the blade shield portion 26) into its FIG. 2 second position as the actuator mechanism 30 is moved from its FIG. 1 first condition and into relatively close proximity to the position assumed when the actuator mechanism 30 is positioned in its FIG. 2 second condition. As will be apparent and within the depicted scalpel 20, the mechanical biasing means 23 is in the form of an over center spring 25 (best shown in FIGS. 12 and 16-19) which is pivotally movable relative to each of the handle member 22 and the actuator mechanism 30 as the actuator mechanism 30 is moved relative to the handle member 22 between the FIG. 1 first condition and the FIG. 2 second condition.

With reference to FIGS. 3-5 and 6-8, the handle member 22 includes an elongated body 32 having opposite front and rear ends 34 and 36, respectively, and two opposite side portions 38 and 40 disposed adjacent the front end 34 of the handle member 22. The handle member 22 is relatively thin as measured transversely, or width-wise, of the body 32 through the opposite side portions 38 and 40 thereof and includes a forwardly-extending blade support 28 to which the blade 24 (FIGS. 1 and 2) is rigidly secured. Inasmuch as the scalpel 20 is intended to be grasped by an operator, or user, as the handle member 22 rests atop of the web of the hand which extends between the thumb and index finger of the grasping hand and the tips of the index finger and thumb of the grasping hand are positioned against the side portions 38 and 40 of the handle member 22 during use, it is preferred that the outer surfaces of the side portions 38 and 40 are provided with a plurality of recesses 41 disposed thereacross to both reduce the likelihood that the scalpel 20 will slip relative to the grasping hand during a surgical, or cutting, procedure and facilitate the manipulation of the handle member 22 during a cutting process performed with the scalpel 20. In addition, the outer surfaces of the side portions 38 and 40 can be roughened or textured to further reduce the likelihood of inadvertent slip of the handle member 22 within the operator's hand while still permitting the handle member 22 to be pivoted, as necessary, about the tips of the fingers and thumb of the grasping hand to alter the angular orientation of the handle member 22 during a cutting process.

In addition, the body 32 of the handle member 22 is provided with an interior 31 provided with upwardly-opening hollow regions disposed between the side portions 38 and 40, and the inside surfaces of the side portions 38, 40 define a pair of inwardly-opening grooves 33 and 35 (FIGS. 14 and 15) which extend longitudinally along the side portions 38 and 40 to facilitate the attachment of the actuator mechanism 30 to the handle member 22. As will be apparent herein and when the scalpel 20 is fully assembled, the actuator mechanism 30 is adapted to cooperate with the grooves 33, 35 which, in turn, serve as parallel guide tracks along which the actuator mechanism 30 is guided as the actuator mechanism 30 is moved substantially linearly along the length of the side portions 38 and 40 between its FIG. 1 first and FIG. 2 second conditions. Further still, there is provided a shelf portion 46 (best shown in FIG. 2) which is formed within so as to extend substantially centrally along the interior 31 of the handle member 22, and the shelf portion 46 defines a forwardly-directed abutment surface 48. As will be apparent herein, this forwardly-directed abutment surface 48 contributes to the capacity of the actuator mechanism 30 to be releasably locked in its FIG. 1, blade-covering condition.

Figure 7:
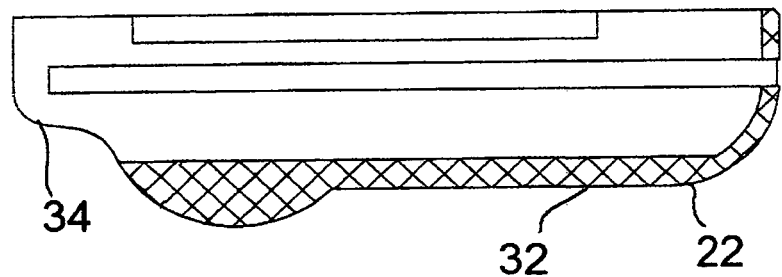
FIG. 7 is a longitudinal cross-sectional view of another fragment of the handle member of the FIG. 1 assembly taken along line 7-7 of FIG. 5.
Figure 8:
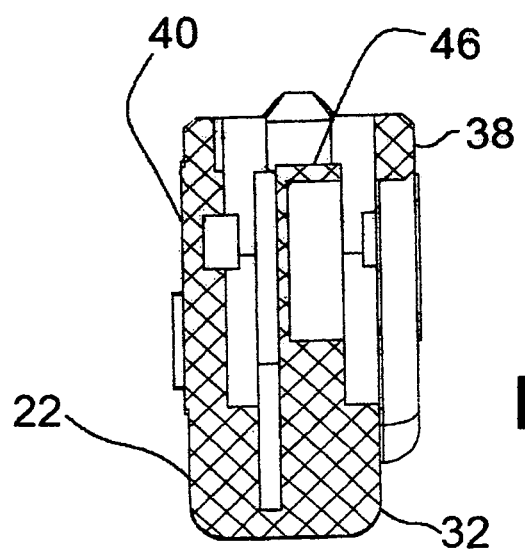
FIG. 8 is a transverse cross-sectional view of the handle member of the FIG. 1 assembly taken along line 8-8 of FIG. 5.

With reference to FIGS. 5 and 7, the hollow regions of the interior 31 are sized to bodily accept the actuator mechanism 30 when the actuator mechanism 30 is connected to the handle member 22 during assembly of the scalpel 20. Furthermore, there is provided along the inside surface of one side portion 38 of the handle member 22 a cutout 43 (FIGS. 6 and 16-18) which is adapted to accept the body of the over center spring 25 when the spring 25 is mounted within the handle member 22 and which is sized to accommodate a readjustment in position, or orientation, of the spring 25 as the spring 25 is pivotally moved between two positions in response to the movement of the actuator mechanism 30 between its first and second conditions. The inside surface of the side portions 38 of the handle member 22 is also provided with an opening 51 (FIG. 6) and in a vertically-disposed groove 53 which leads from the upper surface of the handle member 22 and downwardly to the opening 51. As will be apparent herein, the opening 51 is adapted to accept one end of the spring 25 when the scalpel 20 is assembled, and the groove 53 permits one end of the over center spring 25 to be guided into position into the opening 51 during assembly of the scalpel 20.

If the handle member 22 of the scalpel 20 is not intended to be reused, the body 32 of the handle member 22 is preferably formed (e.g. molded) in one piece out of a hard plastic material, but other materials can be used. In the alternative and if the handle member 22 is intended to be reused, the handle member 22 is preferably constructed out of metal, such as stainless steel.

As best shown in FIG. 5a, the blade 24 of the scalpel 20 is elongated and relatively thin in shape and defines a relatively sharp cutting edge 44 which extends along one of its edges (i.e. the lower edge as viewed in FIG. 5a). As is the case with common scalpel blades, the blade 24 defines an elongated slot 27 which is disposed medially of and extends along the blade body which enables the blade 24 to be secured to the blade support 28. To this end and for purposes of holding a replaceable blade 24, the blade support 28 (FIG. 4) is fashioned with a fitting 17 which is adapted to cooperate with the blade 24 in a manner which is well-known in the art to releasably attach the blade 24 to the blade support 28.

Suffice it to say that in order to secure the blade 24 to the support 28, the blade 24 is positioned against the blade support 28 so that the elongated slot 27 accepts the fitting 17 of the support 28 and so that the blade 24 is thereby rigidly secured to the handle member 22. If the scalpel handle 22 is constructed of plastic and not intended to be reused (i.e. intended to be discarded with the blade following its initial use), the slot 27 of the blade 24 could be first positioned about the fitting 17, and the fitting 17 can be subsequently heated to heat seal the blade 24 in place. The blade 24 is preferably constructed of metal, such as stainless steel, but other materials can be used.

With reference to FIGS. 9-11, the actuator mechanism 30 has an elongated body 50 including a forward section 52 which provides the blade guard portion 26, introduced earlier, of the actuator mechanism 30 and a rearward section 54 including means, generally indicated 56, enabling the actuator mechanism 30 to be releasably connected to the body 32 of the handle member 22 in a manner which accommodates the desired sliding movement of the actuator mechanism 30 relative to and along the length of the handle member 22. In addition, the actuator mechanism 30 includes a latch member 58 disposed between the rearward sections 52, 54 of the actuator mechanism 30 has an upper surface which is capable of being engaged by the index finger of the hand of the user who holds the scalpel 20 for use.

As best shown in FIG. 9, the rearward section 54 of the actuator mechanism 30 has an upper portion 60 which extends along the length of the rearward section 54 and two opposite side portions 62, 64 having lower edges 68, 69, respectively, which depend downwardly from the upper portion 60. The side portions 62, 64 are spaced from one another so as to provide a gap 57 therebetween, and there are provided along the outer surfaces of the side portions 62, 64 outwardly-extending tab portions 70, 72. When the actuator mechanism 30 is connected to the handle member 22, the tab portions 70, 72 are positioned within the grooves 33, 35 of the side portions 38, 40 of the handle member 22 (best shown in FIGS. 14 and 15) to accommodate the sliding movement of the actuator mechanism 30 along the length of the handle member 22 as the grooves 33, 35 and tab portions 70, 72 act as guide rails and guide rail followers, respectively.

Figure 14:
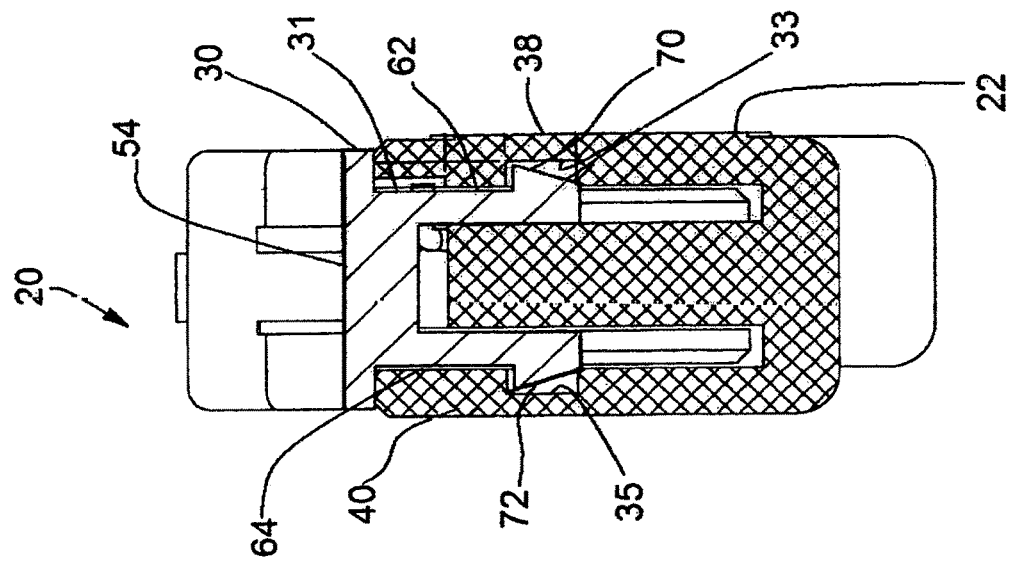
FIG. 14 is a cross-sectional view of the FIG. 1 assembly taken about along line 14-14 of FIG. 1.
Figure 15:
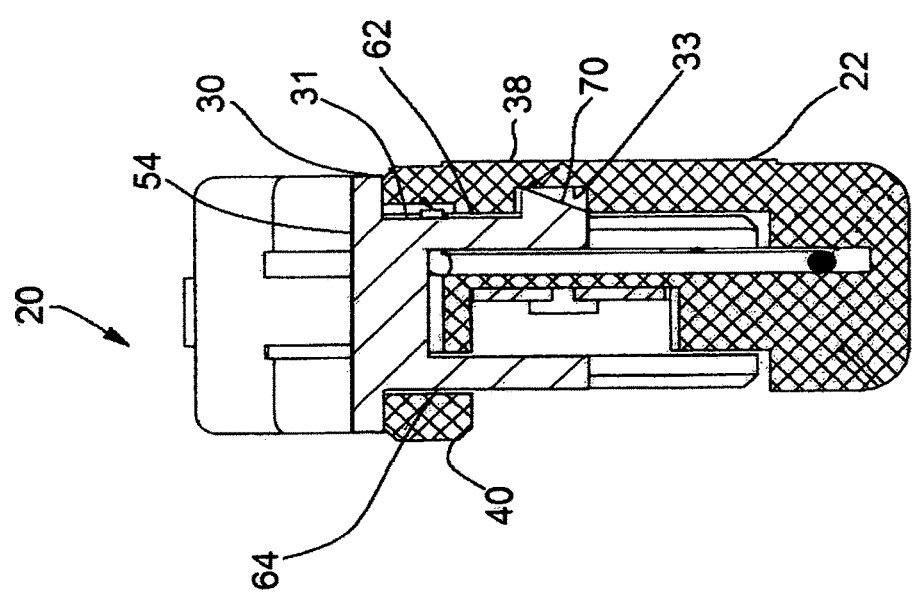
FIG. 15 is a cross-sectional view of the FIG. 1 assembly taken about along line 15-15 of FIG. 1.

In addition, the side portions 62, 64 of the rearward section 54 of the actuator mechanism 30 possess a degree of flexibility and resiliency to accommodate the positioning of the actuator mechanism 30 into snap-fit relationship with the handle member 22 when the tab portions 70, 72 are accepted by the grooves 33, 35 defined within the side portions 38, 40 of the handle member 22. That is to say that when assembling the scalpel 20, the actuator mechanism 30 is disposed above and in vertical registry with the hollow regions of the handle member interior 31 (as depicted in FIG. 13) and then the body 50 of the actuator mechanism 30 is directed downwardly between the side portions 38, 40 of the handle member 22 in a manner which effects the inward flexing of the lower edges 68, 69 of the side portions 62, 64 of the rearward section 54 toward one another. This inward flexing of the side portions 62, 64 permits the tab portions 70, 72 to slide downwardly along the inside surfaces of the side portions 62, 64. When the tab portions 70, 72 reach the grooves 33, 35, the side portions 62, 64 are permitted to return to the undeformed, or unflexed, condition so that the tab portions 70, 72 move away from one another and are accepted by the grooves 33, 35. To this end, the lower surfaces of the tab portions 70, 72 are appropriately sloped (as best shown in FIGS. 14 and 15) to facilitate the movement, or flexing, of the lower edges 68, 69 (FIGS. 9 and 10) of the side portions 62, 64 inwardly toward one another as the tab portions 70, 72 are slidably moved downwardly along the hollow regions of the handle member interior 31, and the material of the actuator mechanism 30 is preferably a plastic material which imparts a desired resiliency to the side portions 38, 40.

Meanwhile and with reference again to FIGS. 9-11, the forward section 52 of the actuator mechanism 30 includes an upper portion 94 which extends longitudinally along the forward end of the actuator mechanism 30 and has two substantially planar side portions 76 and 78 having lower edges 80 and 82, respectively, which depend downwardly from the upper portion 94. The side portions 76, 78 are spaced from one another so as to provide a gap 84 therebetween, and it is the side portions 76, 78 and upper portion 74 which collectively provide a guard which substantially encloses the blade 24 when the actuator mechanism 30 is positioned in its FIG. 1, blade-covering condition. In other words and when the actuator mechanism 30 is positioned within the FIG. 1 blade-guarding condition, the blade 24 is positioned within the gap 84 and straddled by the side portions 76, 78.

With reference again to FIG. 1, the side portions 76, 78 of the forward section 52 of the actuator mechanism 30 are sized with respect to the blade 24 so that when the actuator mechanism 30 is disposed in its FIG. 1 blade-covering condition, the lower edges 80, 82 of the forward section 52 extend forwardly of and below the cutting edge 44 of the blade 24. This being the case and as long as the forward section 52 of the actuator mechanism 30 is positioned in its FIG. 1 blade-covering condition, the cutting edge 44 of the blade 24 is prevented from engaging a surface.

With reference to FIG. 11, the finger-engagable latch member 58 of the actuator mechanism 30 includes a somewhat U-shaped body 88 having a one, or a rearward, leg 90 which is joined in a fixed relationship to the remainder of the actuator mechanism 30 and another, or forward, leg 92 Which is disposed forwardly of the one, or rearward, leg 90. In addition, there is defined along the underside of the U-shaped body 88 a hook portion 95 having a rearwardly-facing abutment surface 96. In addition, the U-shaped body 88 possesses a degree of resiliency and flexibility to permit the forward leg 92 of the U-shaped body 88 to be flexed about the rearward leg 90 between an unflexed condition, as depicted in solid lines in FIG. 11 at which the hook portion 95 is disposed in a lowermost position, and a flexed condition, as depicted in phantom in FIG. 11 at which the hook portion 95 is disposed in a raised, or elevated, position. As will be apparent herein and when the actuator mechanism 30 is disposed in its FIG. 1 blade-covering, condition, the hook portion 95 cooperates with the forwardly-directed abutment surface 48 of the shelf portion 46 of the handle member 22 (depicted in phantom in FIG. 11) to releasably secure the actuator mechanism 30 in its FIG. 1, blade-covering, condition.

The latch member 58 and, more specifically, its U-shaped body 88, can be moved, or raised, from its unflexed condition to its flexed condition with the index finger of the user's hand used to hold the scalpel 20 during use. In other words, the user's index finger which normally overlies the latch member 58 during use of the scalpel 20 can be used to manipulate the U-shaped body from its unflexed condition to its flexed condition by simply pulling the forward leg 92 of the U-shaped body 88 rearwardly of the remainder of the actuator mechanism 30. Since the movement of the actuator mechanism 30 relative to the handle member 22 from its blade-covering condition to its blade-covering condition necessitates the movement of the actuator mechanism 30 rearwardly along the handle member 22, the manipulation, or lifting, of the forward leg 92 of the U-shaped body 88 from its lowered, or unflexed, condition to its raised, or flexed condition, and the subsequent movement of the actuator mechanism 30 along the handle member 22 can be effected in one smooth motion of the index finger.

Further still and with reference still to FIG. 11, there is defined alongside the inside surface of the side portion 76 of the actuator mechanism 30 a bore 104 which, as will be apparent herein, is adapted to accept one end of the over center spring 25 to thereby connect the over center spring 25 to the actuator mechanism 30.

Figure 19:
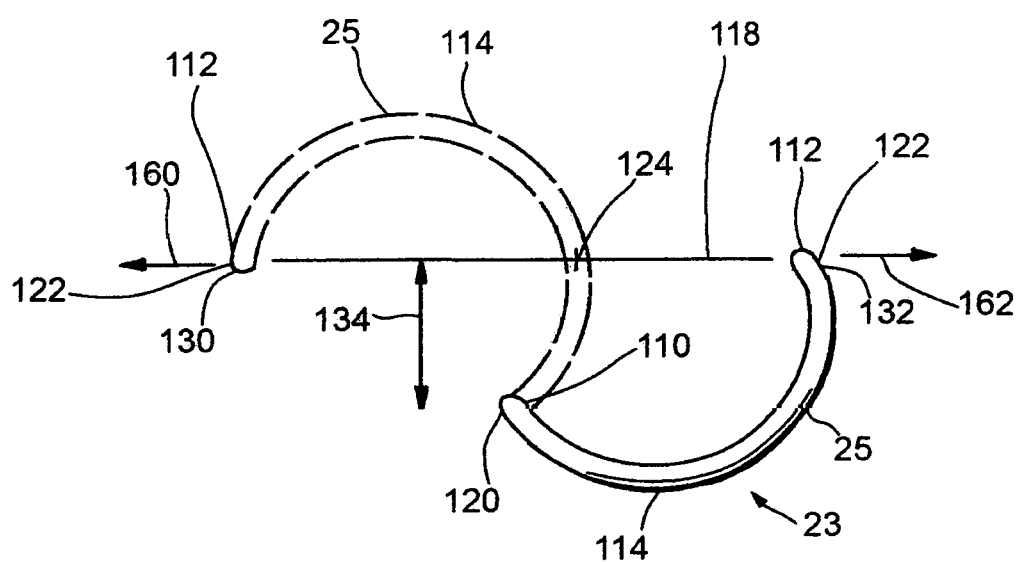
FIG. 19 is a side elevation view illustrating the adjustment in bodily orientation of the over center spring of FIG. 12 when the actuator mechanism of the FIG. 1 assembly is moved from the first condition to the second condition.

With reference to FIGS. 12 and 19, the over center spring 25 has two opposite end portions 110, 112 and a major portion 114 which extends along a C-shaped arcuate path between the end portions 110, 112 and which lies substantially in a single plane. Furthermore and for purposes of connecting the spring end portions 110, 112 between the actuator mechanism 30 and the handle member 22, each end portion 110 or 112 is linear in form and extends away from (i.e. normal to) the plane within which the major portion 114 of the spring 25 is contained and in a direction opposite the direction in which the other end portion 112 or 110 extends. For connection of the spring 25 to the handle member 22, one spring end portion 110 is positioned within the opening 51 (FIG. 6) defined within the side portion 38 of the handle member 22, and the other spring end portion 112 is accepted (endwise) by so as to be positioned within the bore 104 (FIG. 11) provided in the actuator mechanism 30.

To assemble the actuator mechanism 30, the over center spring 25 and the handle member 22 together and with reference to FIG. 13, one end portion 110 of the spring 25 is initially guided downwardly along the groove 53 and is then directed endwise into the opening 51 provided in the handle member 22. With the actuator mechanism 30 arranged in a superposed relationship with the hollow regions of the interior 31 of the handle member 22 (as depicted in FIG. 13), the other end portion 112 of the over center spring 25 is directed endwise into the bore 104 defined alongside the side portion 76 of the actuator mechanism 30 and then the actuator mechanism 30 is directed bodily downwardly into the hollow regions of the interior 31 of the handle member 22 so that the tab portions 70, 72 are slidably moved into snap-fit relationship with the grooves 33, 35 provided within the handle member 22, as best shown in FIGS. 14 and 15. With the tab portions 70, 72 being accepted by the grooves 33, 35 of the handle member 22 (as best shown in FIGS. 14 and 15), the major portion 114 of the over center spring 25 is accepted by the cutout 43 (FIGS. 6 and 16-18) provided alongside the side portion 38.

With the tab portions 70, 72 being accepted by the grooves 33, 35 and the over center spring 25 being connected between the handle member 22 and the actuator member 30 as aforedescribed, the actuator mechanism 30 is free to slidably move along the length of the handle mechanism 22 between the FIG. 1 blade-covering condition and the FIG. 2 out-of-the-way condition, and the over center spring 25 is free to bodily move within the cutout 43 as its major portion 114 pivots about each of its end portions 110, 112. In addition, the body 50 of the actuator mechanism 30 and the body 32 of the handle member 22 confine the spring 25 laterally with respect to the handle member 22 so that the spring end portions 110, 112 are prevented from backing out of the opening 51 and bore 104.

With the actuator mechanism 30 connected to the handle member 22 as aforedescribed so that the over center spring 25 is interposed between the actuator mechanism 30 and the handle member 22, the spring 25 is in a compressed condition so that its end portions 110 and 112 are continually biased apart. Accordingly, the spring 25 is sized so that when positioned with its end portion 110 disposed within the opening 51 of the handle member 22 and its other end portion 112 accepted (endwise) by the bore 104 defined within the actuator mechanism 30, the spring end portions 110 and 112 are continually urged further apart.

Figure 16:
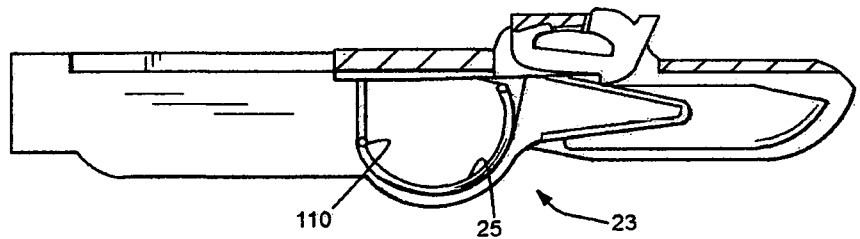
FIG. 16-18 are longitudinal cross-sectional views of fragments of the components of the FIG. 1 assembly schematically illustrating, in sequential views, the positional relationship of the actuator mechanism (and its blade shield portion) of the FIG. 1 assembly as the actuator mechanism is manually moved along the handle member from a FIG. 1 first condition to a FIG. 2 second condition to effect the movement of the blade shield portion from a blade-covering position to an out-of-the-way position.
Figure 17:
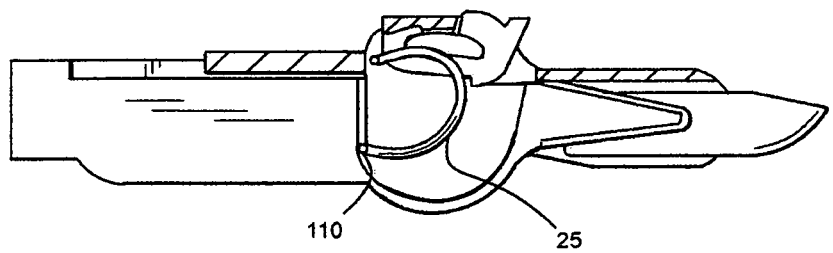
Figure 18:
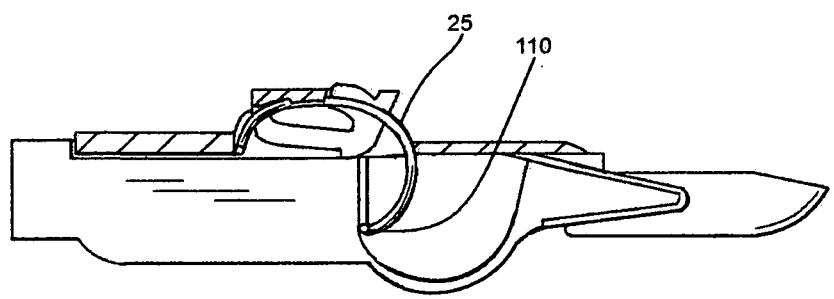

With reference to FIGS. 16-18, there is illustrated the relative disposition of the spring 25, the actuator mechanism 30, and the handle member 22 as the actuator mechanism 30 is moved along the handle member 22 between the FIG. 1 (and FIG. 16) first condition and the FIG. 2 (and FIG. 18) second condition. Within FIGS. 16-18, one spring end portion 110 (positioned within the opening 51 of the handle member 22) is adapted to pivot relative to the handle member 22 about a pivot axis, indicated 120 in FIG. 19, while the other spring end portion 112 (accepted by the bore 104 of the actuator mechanism 30) is adapted to pivot relative to the handle member 22 about a pivot axis, indicated 122 in FIG. 19. It therefore follows that as the actuator mechanism 30 is moved relative to the handle member 22 and linearly along the grooves 33, 35, the pivot axis 122 is moved, or guided, linearly along a path of travel as the pivot axis 120 remains stationary within the handle member 22 and the C-shaped major portion 114 of the spring 25 is bodily rotated about the pivot axis 120.

As an aid to understanding the function of the over center spring 25 within the scalpel 20, there is illustrated in solid lines in FIG. 19 the disposition, or orientation, of the spring 25 in relation to the pivot axes 120, 122 when the actuator mechanism 30 is disposed in its FIG. 1 (and FIG. 16) first condition and there is illustrated in phantom in FIG. 19 the disposition, or orientation, of the spring 25 in relation to the pivot axes 120, 122 when the actuator mechanism 30 is disposed in its FIG. 2 (and FIG. 18) second condition. In this FIG. 19 view, the location of the pivot axis 122 when the actuator mechanism 30 is disposed in its FIG. 1 condition also corresponds with the location of the spring end portion 112 when the actuator mechanism 30 is disposed at its rearwardmost limit of travel along the length of the grooves 33, 35, and this rearwardmost location of travel of the pivot axis 122 is indicated 130 in FIG. 19. By comparison, the location of the pivot axis 122 when the actuator mechanism 30 is disposed in its FIG. 2 second condition also corresponds with the location of the spring end portion 112 when the actuator mechanism 30 is disposed in its forwardmost limit of travel along the length of the grooves 35, 37, and this forwardmost limit of travel of the pivot axis 122 is indicated 132 in FIG. 19. The path of travel of the pivot axis 122 between its rearwardmost and forwardmost limit of travel 130, 132 is indicated 118 in FIG. 19, and the midpoint of the path of travel 118 (i.e. the point located substantially halfway along the length of the path of travel 118) is indicated 124.

As mentioned earlier, the over center spring 25 is in a compressed condition when mounted in an assembled scalpel 20, and such a compressed condition continually urges the opposite end portions 110, 112 of the spring 25 apart. Since the spring end portion 110 remains in a fixed position within the handle member 22 as the actuator mechanism 30 is moved between the FIG. 1 first and the FIG. 2 second conditions, the only movement of the spring end portions 110 and 112 toward and away from one another is effected as the spring end portion 112 travels with the actuator mechanism 30 along the path of travel 118 between the forward and rearward limits of travel 130, 132. Moreover and due to the disposition of the spring end portion 110 relative to the path of travel 118, the closest that the pivot axis 122 ever gets to the pivot axis 120 is when the pivot axis 122 moves to the midpoint 124 of the path of travel 118.

Stated another way, the closest that the pivot axis. 122 ever gets to the pivot axis 120 corresponds with the distance, indicated 134 in FIG. 19, as measured between the pivot axis 120 and the midpoint 124 of the path of travel 118. Consequently, when the pivot axis 122 is positioned at any point rearwardly along the path of travel 118 from the midpoint 124 to the rearwardmost limit of travel 130, the urging apart of the spring end portions 110, 112 due to the compressed condition of the spring 25 induces a force component along the path of travel 118 which is directed rearwardly therealong (i.e. in the direction of the FIG. 19 arrow 160)) and, in turn, urges the actuator mechanism 30 rearwardly (with respect to the handle member 22) along the path of travel 118. By comparison, when the pivot axis 122 is positioned at any point forwardly along the path of travel 118 from the midpoint 124 to the forwardmost limit of travel 132, the urging apart of the spring end portions 110, 112 due to the compressed condition of the spring 25 induces a force component along the path of travel 118 which is directed forwardly therealong (i.e. in the direction of the FIG. 19 arrow 162)) and, in turn, urges the actuator mechanism 30 forwardly (with respect to the handle member 22) along the path of travel 118.

It therefore follows that the over center spring 25 is adapted to act between the actuator mechanism 30 and the handle member 22 so that until the actuator mechanism 30 has been moved forwardly with respect to the actuator mechanism 30 from the FIG. 1 first condition toward the FIG. 2 second condition along the path of travel 118 to about the midpoint 124 thereof (i.e. so that the pivot axis 122 is moved from the FIG. 19 location 130 to the midpoint 124), the movement of the blade shield portion 26 of the actuator mechanism 30 toward the FIG. 2 out-of-the-way position is opposed by the biasing force of the over center spring 25, but upon movement of the actuator mechanism 30 from the FIG. 1 first condition toward the FIG. 2 second condition along the path of travel 118 beyond the midpoint 124 thereof (i.e. so that the pivot axis 122 is moved from the midpoint 124 to the FIG. 19 location 132), the blade shield portion 26 of the actuator mechanism 30 is biased toward the FIG. 2 out-of-the-way position by the biasing force of the over center spring 25. Similarly, until the actuator mechanism 30 has been moved rearwardly with respect to the actuator mechanism 30 from the FIG. 2 second condition toward the FIG. 1 first condition along the path of travel 118 to about the midpoint 124 thereof (i.e. so that the pivot axis 122 is moved from the FIG. 19 location 132 to the midpoint 124), the movement of the blade shield portion 26 toward the FIG. 1 blade-covering position is opposed by the biasing force of the over center spring 25, but upon movement of the actuator mechanism 30 from the FIG. 2 second condition toward the FIG. 1 first condition along the path of travel 118 beyond the midpoint 124 thereof (i.e. so that the pivot axis 122 is moved from the midpoint 124 to the FIG. 19 location 130), the blade shield portion 26 is biased toward the blade-covering position by the biasing force of the over center spring 25.

An advantage provided by the scalpel 20 and its over center spring 25 relates to the maintenance of the blade shield portion 26 in each of its FIG. 1 blade-covering position and its FIG. 2 out-of-the-way position. In other words and because the biasing force of the spring 25 continually acts upon the actuator mechanism 30 (and its blade shield portion 26) while the actuator mechanism 30 is positioned in either of its FIG. 1 first condition or FIG. 2 second condition, the actuator mechanism 30 is firmly maintained in its first or second condition by the spring 25 until such time that the operator desires to manually move (by way of the actuator mechanism 30) the blade shield portion 26 to the other of its blade-covering or out-of-the-way positions.

While the aforedescribed biasing force of the over center spring 25 helps to maintain the actuator mechanism 30 and its blade shield portion 26 within the FIG. 1 blade-covering condition, the hook portion 95 associated with the latch member 58 also helps to prevent the inadvertent movement of the actuator mechanism 30 out of its FIG. 1 blade-covering condition. In this connection and with reference again to FIGS. 11 and 16, when the actuator mechanism 30 is positioned in its forwardmost position along the length of the handle member 22 (which position corresponds to the position assumed by the actuator mechanism 30 when in its FIG. 1 blade-covering condition), the hook portion 95 associated with the latch member 58 is hooked about the forwardly-directed abutment surface 48 of the shelf portion 46 of the handle member 22 (with the abutment surface 96 in engagement with the abutment surface 48) to releasably lock the actuator mechanism 30 in its forwardmost, or blade-covering, condition along the length of the handle member 22.

To release the latch member 58 from the locked condition with the shelf portion 96, the latch member 58 is pulled rearwardly by the index finger so that the forward leg 92 of the latch member 58 is lifted, or flexed, to its raised (or FIG. 11 phantom-line) condition to subsequently permit the actuator mechanism 30 to clear (the uppermost edge) of the abutment surface 48 and subsequently be moved rearwardly along the length of the handle member 22. It follows that with the latch member 58 positioned in its raised condition, its hook portion 95 is in condition to be moved (i.e. slid) along the length of the upper surface of the shelf portion 46 of the handle member 22 as the actuator mechanism 30 is moved forwardly or rearwardly along the length of the handle member 30 between the FIG. 1 blade-covering condition and the FIG. 2 blade-exposing condition. To promote the useful life of the latch member 58, the upper surface of the shelf portion 46 is sloped downwardly from the abutment surface 48 so that when the actuator member 30 is eventually moved into the FIG. 1 blade-covering condition, the latch member 58 is returned to its lowered, or unflexed—and thus unstressed, condition.

Another advantage provided by the scalpel 20 relates to the amount of finger displacement required by operator to manually move the actuator mechanism 30 between the FIG. 1 first condition and the FIG. 2 second condition. In this regard and as mentioned earlier, upon movement of the actuator mechanism 30 along the path of travel 118 (FIG. 16) beyond the midpoint, the biasing force of the spring 25 biases (and thereby aids the movement of) the actuator mechanism 30 in the corresponding (e.g. desired) direction of movement along the path of travel 118. In practice, the biasing force of the spring 25 has been found to be of sufficient strength to automatically move the actuator mechanism 20 toward the desired FIG. 1 first or FIG. 2 second condition without aid of the operator's finger—once the actuator mechanism 30 has been moved beyond the midpoint 124 of the path of travel 118. Therefore and to move the blade shield portion 26 to either its FIG. 1 blade-covering position or its FIG. 2 out-of-the-way position, the operator need only move the actuator mechanism 30 from the FIG. 1 first or FIG. 2 second condition along the path of travel to a point just beyond the midpoint 124 thereof, because at that point, the biasing force of the spring 25 is sufficient to continue the movement of the actuator mechanism 30 to the desired first or second condition. Accordingly and to move, or flip, the blade shield portion 26 from one of its blade-covering or out-of-the-way condition to the other of its blade-covering or out-of-the-way condition, the operator need only use his index finger to displace the actuator mechanism 30 by a little more than one-half the length of the path of travel 118, and the scalpel 20 is advantageous in this respect.

Still another advantage provided by the scalpel 20 relates to its relatively few number of components. More specifically and when compared to some common scalpel assemblies whose blades are covered by a movable blade-protecting shield involving many components, the depicted scalpel 20 has relatively few components.

It follows from the foregoing that a scalpel handle-providing means (or handle) 18 has been described for holding a blade 24 having a cutting edge 44 which includes a handle member 22 and a finger-engageable actuator mechanism 30 having a blade shield portion 26 for covering, when desired, the blade cutting edge 44. The actuator mechanism 30 is mounted upon the handle member 22 for sliding movement relative thereto between a first (i.e. rearwardly-disposed) condition and a second (i.e. forwardly-disposed) condition, and the over center spring 25 is interposed between the actuator mechanism 30 and the handle member 22 so that upon movement of the actuator mechanism 30 from its first condition into the position assumed by the actuator mechanism 30 when in its second condition, the blade shield portion 26 of the actuator mechanism 30 is biased by the over center spring 25 into the out-of-the-way position. Furthermore and upon movement of the actuator mechanism 30 from its second condition into the position assumed by the actuator mechanism 30 when in its first condition, the blade shield portion 26 of the actuator mechanism 30 is biased by the over center spring 25 into the blade-covering position.

It will be understood that numerous modifications and substitutions can be had to the aforedescribed embodiment 20 without departing from the spirit of the invention. Accordingly, the aforedescribed embodiment 20 is intended for the purpose of illustration and not as limitation.

The invention claimed is:

1. A scalpel handle for holding a blade having a cutting edge, the scalpel handle comprising:
   a handle member to which a blade is securable for use;
   a manually-operable actuator mechanism having a blade shield portion which is mounted upon the handle member for movement relative thereto between a first condition and a second condition and along a substantially linear path of movement so that when a blade is secured to the handle member and the actuator mechanism is positioned in the first condition, the blade shield portion is positioned in a blade-covering position at which the cutting edge of the blade is covered by the blade shield portion and when the actuator mechanism is positioned in the second condition, the blade shield portion is positioned in an out-of-the-way position which exposes the cutting edge of the blade for use; and
   an over center spring having two opposite end portions and being interposed between the actuator mechanism and the handle member so that upon movement of the actuator mechanism from the first condition into the position assumed by the actuator mechanism when in the second condition, the blade shield portion is biased by the over center spring into the blade-exposing position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield portion is biased by the over center spring into the blade-covering position and the over center spring resists movement of the actuator mechanism from the first condition toward the position assumed by the actuator mechanism when in the second condition
   wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the substantially linear path of movement, the one end portion of the over center spring also moves along a substantially linear path of movement; and
   wherein the over center spring is adapted to pivot about one of the two end portions of the over center spring when the actuator mechanism is moved between the first condition and the second condition.

2. The scalpel handle as defined in claim 1 wherein one of the actuator mechanism and the handle member includes a tab portion and the other of the actuator mechanism and the handle member includes a guide track along which the tab portion is slidably positioned so that as the actuator mechanism is moved relative to the handle member between the first and second conditions, the actuator mechanism is moved along the substantially linear path of movement as the tab portion is guided along the guide track.

3. The scalpel handle as defined in claim 1 wherein the actuator mechanism is adapted to move in a first direction along the substantially linear path of movement when the actuator mechanism is moved from the first condition toward the second condition, and wherein the over center spring is adapted to act between the actuator mechanism and the handle member so that until the actuator mechanism is moved in the first direction along the path of movement toward the second condition by a predetermined interval, the over center spring opposes the movement of the actuator mechanism in the first direction but upon movement of the actuator mechanism in the first direction along the substantially linear path of movement beyond the predetermined interval, the over center spring biases the actuator mechanism toward the second condition.

4. The scalpel handle as defined in claim 3 wherein the substantially linear path of movement along which the actuator mechanism is adapted to move is a first path of movement and the actuator mechanism is adapted to move relative to the handle member from a first limit of travel to a second limit of travel as the actuator mechanism is moved along the first path of movement from the first condition to the second condition and the first path of movement has a midpoint located substantially midway between the first and second limits of travel, and the predetermined interval substantially corresponds with the distance moved by the actuator mechanism from the first condition to the midpoint of the first path of movement.

5. The scalpel handle as defined in claim 1 wherein the substantially linear path of movement along which the actuator mechanism is adapted to move is a first path of movement and the actuator mechanism is mounted upon the handle member for movement relative thereto from the first condition to the second condition along the first path of movement and between first and second limits of travel, and the first path of movement has a midpoint located substantially midway along the length of the first path of movement, and the over center spring is adapted to act between the actuator mechanism and the handle member so that until the actuator mechanism has been moved from the first condition along the first path of movement to about the midpoint of the first path of movement, the movement of the actuator mechanism toward the second condition is opposed by the biasing force of the over center spring, but upon movement of the actuator mechanism from the first condition along the first path of movement beyond the midpoint of the first path of movement, the actuator mechanism is biased toward the out-of-the-way position by the biasing force of the over center spring.

6. The scalpel handle as defined in claim 1 wherein the over center spring has a major portion which extends between the two opposite end portions which is substantially C-shaped in form.

7. The scalpel handle as defined in claim 1 wherein the over center spring is mounted within the handle member so that upon movement of the actuator mechanism to the second condition, the over center spring is in a compressed condition which biases the opposite end portions of the spring further apart to thereby bias the actuator mechanism into the second condition.

8. The scalpel handle as defined in claim 1 wherein the scalpel handle is adapted to be held between the thumb and the fingers of a hand which grasps the scalpel handle for use and the actuator mechanism includes a finger-engagable portion which is engagable by the tip of the index finger of the hand which grasps the handle member for moving the actuator mechanism relative to the handle member between the first and second conditions, and the finger-engagable portion is adapted to cooperate with the handle member to releasably lock the actuator mechanism in the first condition to thereby prevent inadvertent movement of the actuator mechanism out of the first condition.

9. A scalpel handle for holding a blade having a cutting edge, the scalpel handle comprising:
   a handle member to which a blade is securable for use;
   a manually-operable actuator mechanism which is mounted upon the handle member for movement relative thereto between a first condition and a second condition and along a first substantially linear path of movement and including a blade shield portion, wherein the actuator and the blade shield portion are capable of movement relative to and along the handle member between a blade-covering position at which the blade shield portion covers the cutting edge of the blade and an out-of-the way position at which the cutting edge of the blade is exposed for use and so that by moving the actuator mechanism from the first condition toward the second condition, the blade shield portion is moved from the blade-covering position toward the out-of-the-way position and so that by moving the actuator mechanism from the second condition toward the first condition, the blade shield portion is moved from the out-of-the-way position toward the blade-covering position; and
   an over center spring having two opposite end portions and being interposed between the actuator mechanism and the handle member so that upon movement of the actuator mechanism from the first condition into the position assumed by the actuator mechanism when in the second condition, the blade shield portion is biased by the over center spring into the out-of-the-way position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield portion is biased by the over center spring into the blade-covering position and the action of the over center spring resists movement of the actuator mechanism out of the first condition and toward the position assumed by the actuator mechanism when in the second condition,
   wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the first substantially linear path of movement, the one end portion of the over center spring also moves along a substantially linear path of movement; and
   wherein one of the actuator mechanism and the handle member includes a tab portion and the other of the actuator mechanism and the handle member includes a guide track along which the tab portion is slidably received so that as the actuator mechanism is moved relative to the handle member between the first and second conditions, the actuator mechanism is moved along the first substantially linear path of movement as the tab portion is guided along the guide track; and
   wherein the over center spring is adapted to pivot about one of the two end portions of the over center spring when the actuator mechanism is moved between the first condition and the second condition.

10. The scalpel handle as defined in claim 9 wherein the over center spring is mounted within the scalpel handle so that when the actuator mechanism is moved into the second condition from the first condition or into the first condition from the second condition, the spring is in a compressed condition which biases the opposite end portions of the over center spring further apart.

11. The scalpel handle as defined in claim 9 wherein the actuator mechanism is adapted to move along the first path of movement as the actuator mechanism is moved between the first condition and the second condition wherein the actuator mechanism is adapted to move in a first direction along the first path of movement when the actuator mechanism is moved from the first condition toward the second condition and is adapted to move in a second direction along the first path of movement when the actuator mechanism is moved from the second condition toward the first condition, and wherein the over center spring is adapted to act between the actuator mechanism and the handle member so that until the actuator mechanism is moved in the first direction along the first path of movement toward the second condition by a predetermined interval, the over center spring opposes the movement of the actuator mechanism in the first direction but upon movement of the actuator mechanism in the first direction along the first path of movement beyond the predetermined interval, the over center spring biases the actuator mechanism and the blade shield portion into the out-of-the-way position and so that until the actuator mechanism is moved in the second direction along the first path of movement toward the first condition by a predetermined distance, the over center spring opposes the movement of the actuator mechanism in the second direction but upon movement of the actuator mechanism in the second direction along the first path of movement beyond the predetermined distance, the over center spring biases the actuator mechanism and the blade shield portion into the blade-covering position.

12. The scalpel handle as defined in claim 11 wherein the actuator mechanism is adapted to move relative to the handle member along the first path of movement between a first limit of travel and a second limit of travel as the actuator mechanism is moved between the first condition and the second condition and the first path of movement has a midpoint located substantially midway between the first and second limits of travel, and the predetermined interval substantially corresponds with the distance moved by the actuator mechanism in the first direction from the first condition to the midpoint of the first path of movement and the predetermined distance substantially corresponds with the distance moved by the actuator mechanism in the second direction from the second condition to the midpoint of the first path of movement.

13. The scalpel handle as defined in claim 9 wherein the actuator mechanism is mounted upon the handle member for movement relative thereto between the first condition and the second condition along the first path of movement and between first and second limits of travel, and the first path of movement has a midpoint located substantially midway along the length of the first path of movement, and the over center spring is adapted to act between the actuator mechanism and the handle member so that until the actuator mechanism has been moved from the first condition toward the second condition along the first path of movement to about the midpoint of the first path of movement, the movement of the blade shield portion toward the out-of-the-way position is opposed by the biasing force of the over center spring, but upon movement of the actuator mechanism from the first condition toward the second condition along the first path of movement beyond the midpoint of the first path of movement, the actuator mechanism is biased toward the out-of-the-way position by the biasing force of the over center spring and so that until the actuator mechanism has been moved from the second condition toward the first condition along the first path of movement to about the midpoint of the first path of movement, the movement of the actuator mechanism and the blade shield portion toward the blade-covering position is opposed by the biasing force of the over center spring, but upon movement of the actuator mechanism from the second condition toward the first condition along the first path of movement beyond the midpoint of the first path of movement, the actuator mechanism and the blade shield portion is biased toward the blade-covering position by the biasing force of the over center spring.

14. The scalpel handle as defined in claim 9 wherein the over center spring is mounted within the scalpel handle so that upon movement of the actuator mechanism into the second condition, the over center spring is disposed in a compressed condition which biases the two end portions of the spring apart and thus biases the actuator mechanism into the second condition and so that upon movement of the actuator mechanism into the first condition, the over center spring is disposed in a compressed condition which biases the two end portions of the spring apart and thus biases the actuator mechanism into the first condition.

15. The scalpel handle as defined in claim 14 wherein the actuator mechanism is mounted for movement relative to the handle member along the first substantially linear path of movement between a first limit of travel which corresponds to the first condition of the actuator mechanism and a second limit of travel which corresponds to the second condition of the actuator mechanism, and the first path of movement has a midpoint which is located substantially between the first and second limits of travel and said one end of the two opposite ends of the spring is adapted to act against the handle member at a preselected location thereon wherein said preselected location is closest to the first path of movement at the midpoint thereof so that when the actuator mechanism is disposed at any location along the first path of movement between the midpoint thereof and the second condition, the compressed condition of the spring biases the actuator and the blade shield portion toward the out-of-the-way position and so that when the actuator mechanism is disposed at any location along the first path of movement between the midpoint thereof and the first condition, the compressed condition of the spring biases the actuator mechanism and the blade shield portion toward the blade-covering position.

16. A scalpel handle for holding a blade having a cutting edge, the scalpel handle comprising:
an elongated handle member to which a blade is securable for use and which is capable of being held between the thumb and fingers of a hand which may grasp the handle member, the handle member having a forward end and a rearward end and the blade is securable to the handle member so that the blade extends substantially forwardly of the handle member;

a manually-operable actuator mechanism having a blade shield portion which is mounted upon the handle member for movement relative thereto between a first condition and a second condition and along a substantially linear path of movement so that when a blade is secured to the handle member and the actuator mechanism is positioned in the first condition, the blade shield portion of the actuator mechanism is positioned in a blade-covering position at which the cutting edge of the blade is covered by the blade shield portion and so that when the actuator mechanism is positioned in the second condition, the blade shield portion of the actuator mechanism is positioned in an out-of-the-way position which exposes the cutting edge of the blade for use; and an over center spring having two opposite end portions and being interposed between the actuator mechanism and the handle member so that upon movement of the actuator mechanism from the first condition into the position assumed by the actuator mechanism when in the second condition, the blade shield portion is biased by the over center spring into the blade-covering condition and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield portion is biased by the over center spring into the blade-covering position and the over center spring resists movement of the actuator mechanism from the first condition toward the position assumed by the actuator mechanism when in the second condition wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the substantially linear path of movement, the one end portion of the over center spring also moves along a substantially linear path of movement, wherein the over center spring is adapted to pivot about one of the two end portions of the over center spring when the actuator mechanism is moved between the first condition and the second condition; and the actuator mechanism includes a finger-engageable portion which is engageable by the tip of the index finger of the hand which grasps the handle member for moving the actuator mechanism during use, and the finger-engageable portion is adapted to cooperate with the handle member to releasably lock the actuator mechanism in the first condition to prevent inadvertent movement of the actuator mechanism out of the first condition.

17. The scalpel handle as defined in claim 16 wherein the handle member includes an abutment surface which faces substantially forwardly of the handle member, and the finger-engageable portion includes a latch member which is adapted to engage the abutment surface of the handle member when the actuator mechanism is in the first condition so that until the latch member is disengaged from the abutment surface, the actuator mechanism is prevented from moving from the first condition toward the second condition.

18. The scalpel handle as defined in claim 17, wherein the finger-engageable portion is adapted to be disengaged from the abutment surface with the tip of the index finger of the hand which grasps the handle member as the tip of the index finger moves the latch member out of engagement with the abutment surface.

19. The scalpel handle as defined in claim 18 wherein the finger-engageable portion is comprised of a resiliently flexible material and is joined to the remainder of the actuator mechanism in a manner which accommodates a flexing of the finger-engageable portion between a first position at which the stop portion bears against the abutment surface and a second condition at which the latch member is disengaged from the abutment surface.

20. A scalpel assembly comprising:
a blade having a cutting edge;
a handle member to which the blade is secured;
a manually-operable actuator mechanism which is mounted upon the handle member for movement relative thereto between a first condition and a second condition and along a substantially linear path of movement and including a blade shield portion, wherein the actuator mechanism is connected to the handle member for movement of the blade shield portion relative to the handle member between a blade-covering position at which the blade shield portion covers the cutting edge of the blade and an out-of-the way position at which the cutting edge of the blade is exposed for use and so that by moving the actuator mechanism from the first condition toward the second condition, the blade shield portion is moved from the blade-covering position toward the out-of-the-way position and so that by moving the actuator mechanism from the second condition toward the first condition, the blade shield portion is moved from the out-of-the-way position toward the blade-covering position; and an over center spring having two opposite end portions and being interposed between the actuator mechanism and the handle member so that upon movement of the actuator mechanism from the first condition into the position assumed by the actuator mechanism when in the second condition, the blade shield portion is biased by the over center spring into the out-of-the-way position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield portion is biased by the over center spring into the blade-covering position and the over center spring resists movement of the actuator mechanism from the first condition toward the position assumed by the actuator mechanism when in the second condition, wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the first substantially linear path of movement, the one end portion of the over center spring also moves along a substantially linear path of movement; and wherein the over center spring is adapted to pivot about one of the two end portions of the over center spring when the actuator mechanism is moved between the first condition and the second condition.

* * * * *